(12) United States Patent
Spiegel et al.

(10) Patent No.: US 10,813,743 B2
(45) Date of Patent: Oct. 27, 2020

(54) SOFT TISSUE REPAIR GRAFTS AND PROCESSES FOR PREPARING AND USING SAME

(71) Applicants: Musculoskeletal Transplant Foundation, Edison, NJ (US); The Methodist Hospital, Houston, TX (US)

(72) Inventors: Aldona Jedrysiak Spiegel, Houston, TX (US); Kai-Roy Wang, Jersey City, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 31 days.

(21) Appl. No.: 16/125,435

(22) Filed: Sep. 7, 2018

(65) Prior Publication Data
US 2020/0078165 A1 Mar. 12, 2020

(51) Int. Cl.
*A61F 2/12* (2006.01)
*A61F 2/00* (2006.01)

(52) U.S. Cl.
CPC .............. *A61F 2/12* (2013.01); *A61F 2/0059* (2013.01); *A61F 2/0063* (2013.01); *A61L 2300/406* (2013.01); *A61L 2430/04* (2013.01)

(58) Field of Classification Search
CPC ........................................................ A61F 2/12
USPC .......................................................... 623/7–8
See application file for complete search history.

(56) References Cited

U.S. PATENT DOCUMENTS

| | | | |
|---|---|---|---|
| 4,627,429 A | 12/1986 | Tsuk | |
| 4,776,853 A | 10/1988 | Klement et al. | |
| D298,355 S | 11/1988 | Young | |
| 4,917,112 A | 4/1990 | Katt | |
| 5,314,471 A | 5/1994 | Brauker et al. | |

(Continued)

FOREIGN PATENT DOCUMENTS

| | | |
|---|---|---|
| AU | 201911154 | 4/2019 |
| CN | 104640577 | 5/2015 |

(Continued)

OTHER PUBLICATIONS

U.S. Appl. No. 12/964,250, filed Dec. 9, 2010.

(Continued)

*Primary Examiner* — Suzette J Gherbi
(74) *Attorney, Agent, or Firm* — Cole Schotz, P.C.; Marcella M. Bodner

(57) ABSTRACT

Soft tissue repair grafts are provided for supporting, covering, and/or retaining an implant positioned in the body of a subject. The grafts are particularly suitable for use for pre-pectoral breast reconstruction with a breast implant or tissue expander. The grafts include positional notches for more accurate positioning in a subject. The grafts also include at least one cuff element which is folded to form a reinforced folded edge for suturing the graft more securely to adjacent tissues than previously known grafts. The grafts also include a plurality of arcuate slots which form a plurality of circular patterns arranged concentrically about a focal point, thereby enabling the grafts to expand without tearing and to conform more closely to the implant and/or adjacent body tissues such as the breast pocket, than previously known grafts. Acellular dermal matrices are particularly suitable for making the soft tissue repair grafts.

19 Claims, 5 Drawing Sheets

(56) References Cited

U.S. PATENT DOCUMENTS

| | | |
|---|---|---|
| 5,336,616 A | 8/1994 | Livesey et al. |
| 5,344,454 A | 9/1994 | Clarke et al. |
| 5,453,278 A | 9/1995 | Chan et al. |
| 5,545,233 A | 8/1996 | Neuenfeldt et al. |
| 5,593,440 A | 1/1997 | Brauker et al. |
| 5,653,756 A | 8/1997 | Clarke et al. |
| 5,713,888 A | 2/1998 | Neunfeldt et al. |
| 5,733,336 A | 3/1998 | Neuenfeldt et al. |
| 5,741,330 A | 4/1998 | Brauker et al. |
| 5,782,912 A | 7/1998 | Brauker et al. |
| 5,800,529 A | 9/1998 | Brauker et al. |
| D404,134 S | 1/1999 | Dunshee |
| 5,882,354 A | 3/1999 | Brauker et al. |
| 5,964,804 A | 10/1999 | Brauker et al. |
| 6,293,970 B1 | 9/2001 | Wolfinbarger et al. |
| D452,121 S | 12/2001 | Teichelman |
| 6,497,875 B1 | 12/2002 | Sorrell |
| 6,616,685 B2 * | 9/2003 | Rousseau ............... A61F 2/0063 606/151 |
| 6,734,018 B2 | 5/2004 | Wolfinbarger et al. |
| 6,743,574 B1 | 6/2004 | Wolfinbarger et al. |
| 6,773,458 B1 | 8/2004 | Brauker et al. |
| 6,866,686 B2 | 3/2005 | Ollerenshaw et al. |
| 6,933,326 B1 | 8/2005 | Griffey et al. |
| 7,049,478 B1 | 5/2006 | Smith |
| D537,948 S | 3/2007 | Smith |
| 7,358,284 B2 | 4/2008 | Griffey et al. |
| 7,476,249 B2 | 1/2009 | Frank |
| 7,582,309 B2 | 9/2009 | Rosenberg et al. |
| D609,802 S | 2/2010 | Harren |
| 7,723,108 B2 | 5/2010 | Truncale et al. |
| 7,799,325 B2 | 9/2010 | Kleinsek et al. |
| 7,875,074 B2 | 1/2011 | Chen et al. |
| 7,927,414 B2 | 4/2011 | Yang et al. |
| 8,007,531 B2 | 8/2011 | Frank |
| 8,067,149 B2 | 11/2011 | Livesey et al. |
| 8,197,542 B2 | 6/2012 | Becker |
| 8,202,317 B2 | 6/2012 | Becker |
| 8,263,101 B2 | 9/2012 | Owens et al. |
| 8,268,361 B2 | 9/2012 | Ahlfors |
| 8,324,449 B2 | 12/2012 | McQuillen et al. |
| 8,343,717 B2 | 1/2013 | Owens et al. |
| 8,415,159 B2 | 4/2013 | Ward et al. |
| 8,425,600 B2 | 4/2013 | Maxwell |
| D683,858 S | 6/2013 | Smith |
| 8,486,616 B2 | 7/2013 | Owens et al. |
| 8,557,581 B2 | 10/2013 | Ngo et al. |
| 8,563,232 B2 | 10/2013 | Wolfinbarger et al. |
| 8,563,234 B2 | 10/2013 | Tousimis |
| D693,888 S | 11/2013 | Webster |
| 8,623,398 B2 | 1/2014 | Altman et al. |
| 8,628,791 B2 | 1/2014 | Altman et al. |
| 8,633,027 B2 | 1/2014 | Altman et al. |
| 8,676,899 B2 | 2/2014 | Maxwell |
| 8,685,426 B2 | 4/2014 | Altman et al. |
| D705,429 S | 5/2014 | Cheney |
| 8,735,054 B1 | 5/2014 | Sun et al. |
| 8,746,014 B2 | 6/2014 | Montarino |
| 8,758,781 B2 | 6/2014 | Ward et al. |
| 8,764,824 B2 | 7/2014 | Ledergerber |
| 8,764,825 B2 | 7/2014 | Ledergerber |
| 8,777,965 B2 | 7/2014 | Chen |
| 8,784,486 B2 * | 7/2014 | Schuessler ............... A61F 2/12 623/8 |
| 8,784,499 B2 | 7/2014 | Owens et al. |
| 8,802,920 B2 | 8/2014 | McQuillan et al. |
| 8,858,629 B2 | 10/2014 | Moses et al. |
| 8,858,647 B2 | 10/2014 | Markman |
| 8,916,742 B2 | 12/2014 | Smith |
| 8,936,651 B2 | 1/2015 | Yang |
| 8,986,377 B2 | 3/2015 | Richter et al. |
| 9,027,213 B2 | 5/2015 | Tousimis |
| 9,050,177 B2 | 6/2015 | Markman |
| 9,066,884 B2 | 6/2015 | Altman et al. |
| 9,078,731 B2 | 7/2015 | Montarino |
| 9,089,501 B2 | 7/2015 | Altman |
| 9,089,523 B2 | 7/2015 | Xu et al. |
| 9,114,003 B2 | 8/2015 | Kalus |
| 9,150,318 B1 | 10/2015 | Sun et al. |
| 9,162,011 B2 | 10/2015 | Stillwell et al. |
| 9,180,143 B2 | 11/2015 | Bolland et al. |
| 9,199,002 B2 | 12/2015 | Mao et al. |
| 9,204,953 B2 | 12/2015 | Montarino |
| 9,204,954 B2 | 12/2015 | Montarino |
| 9,206,442 B2 | 12/2015 | Chen |
| 9,220,259 B2 | 12/2015 | Owens et al. |
| 9,238,793 B2 | 1/2016 | Chen et al. |
| 9,271,821 B2 | 3/2016 | Roock et al. |
| 9,277,986 B2 | 3/2016 | Moses et al. |
| 9,308,070 B2 | 4/2016 | Montarino |
| 9,326,840 B2 | 5/2016 | Mortarino |
| 9,336,435 B1 | 5/2016 | Ozog |
| 9,351,819 B2 | 5/2016 | Harper |
| 9,370,536 B2 | 6/2016 | Sun et al. |
| 9,375,017 B2 | 6/2016 | Hazylett et al. |
| 9,375,513 B2 | 6/2016 | Sun et al. |
| 9,382,422 B2 | 7/2016 | Owens |
| 9,426,980 B2 | 8/2016 | Tousimis |
| 9,504,770 B2 | 11/2016 | Xu et al. |
| 9,532,863 B2 | 1/2017 | Hayzlett |
| 9,532,866 B2 | 1/2017 | Kim et al. |
| 9,539,086 B2 | 1/2017 | Schuessler et al. |
| 9,549,805 B2 | 1/2017 | Hayzlett et al. |
| 9,549,812 B2 | 1/2017 | Shetty et al. |
| 9,579,420 B2 | 2/2017 | Wolfinbarger et al. |
| 9,585,744 B2 | 3/2017 | Moses et al. |
| 9,585,986 B2 | 3/2017 | Wolfinbarger et al. |
| 9,592,254 B2 | 3/2017 | Monteiro et al. |
| 9,592,278 B2 | 3/2017 | Sun et al. |
| 9,622,845 B2 | 4/2017 | Markman |
| 9,622,854 B2 | 4/2017 | Markman |
| 9,636,435 B2 | 5/2017 | Sun et al. |
| 9,681,941 B2 | 6/2017 | Griffin et al. |
| 9,782,436 B2 | 10/2017 | Sun |
| 9,808,338 B2 | 11/2017 | Schuessler et al. |
| 9,888,999 B2 | 2/2018 | Forsell et al. |
| 9,901,440 B2 | 2/2018 | Liu et al. |
| 9,936,688 B2 | 4/2018 | Wolfingarger et al. |
| 9,956,072 B2 | 5/2018 | Diaz et al. |
| 9,956,316 B2 | 5/2018 | Chen |
| 9,957,477 B2 | 5/2018 | Chen et al. |
| 9,999,637 B2 | 6/2018 | Owens et al. |
| 10,004,590 B2 | 6/2018 | Shetty et al. |
| 10,022,214 B2 | 7/2018 | Hayzlett |
| 10,039,633 B2 | 8/2018 | Ansorge et al. |
| RE47,100 E | 10/2018 | Smith |
| D841,172 S | 2/2019 | Bannwart |
| 10,231,874 B2 | 3/2019 | Mumby |
| 10,238,485 B2 | 3/2019 | Locarno et al. |
| D851,261 S | 6/2019 | Ricks |
| D856,517 S | 8/2019 | Spiegel et al. |
| D875,957 S | 2/2020 | Bannwart |
| D876,645 S | 2/2020 | Zhang |
| D876,646 S | 2/2020 | Kase |
| D879,978 S | 3/2020 | Bannwart |
| 2003/0083752 A1 | 5/2003 | Wolfinbarger et al. |
| 2004/0162512 A1 * | 8/2004 | Liedtke ............... A61F 13/0203 602/59 |
| 2004/0260315 A1 | 12/2004 | Dell et al. |
| 2005/0028228 A1 | 2/2005 | McQuillan et al. |
| 2005/0186286 A1 | 8/2005 | Takami |
| 2005/0246035 A1 | 11/2005 | Wolfinbarger et al. |
| 2006/0210960 A1 | 9/2006 | Livesey et al. |
| 2007/0207125 A1 | 9/2007 | Bothwell et al. |
| 2007/0244568 A1 | 10/2007 | Matsuda et al. |
| 2007/0269791 A1 | 11/2007 | Takami et al. |
| 2008/0058692 A1 * | 3/2008 | Propp ................. A61F 13/0203 602/54 |
| 2008/0097601 A1 | 4/2008 | Codori-Hurff et al. |
| 2008/0154366 A1 | 6/2008 | Frank |
| 2008/0281419 A1 | 11/2008 | Matheny et al. |
| 2009/0065014 A1 | 3/2009 | Nagata |
| 2009/0198332 A1 | 8/2009 | Becker |
| 2009/0198333 A1 | 8/2009 | Becker |

(56) References Cited

U.S. PATENT DOCUMENTS

| | | |
|---|---|---|
| 2009/0312685 A1 | 12/2009 | Olsen |
| 2010/0003306 A1 | 1/2010 | Von Waldberg-Zeil |
| 2010/0010627 A1 | 1/2010 | Mathey |
| 2010/0028396 A1 | 2/2010 | Ward et al. |
| 2010/0040687 A1 | 2/2010 | Pedrozo et al. |
| 2010/0067106 A1 | 3/2010 | Woker et al. |
| 2010/0082048 A1* | 4/2010 | Granja Filho ......... A61B 17/11 606/153 |
| 2010/0112543 A1 | 5/2010 | Ngo et al. |
| 2010/0191330 A1 | 7/2010 | Lauryssen |
| 2010/0216206 A1 | 8/2010 | Marzaro |
| 2010/0272782 A1 | 10/2010 | Owens et al. |
| 2010/0285587 A1 | 11/2010 | Ollerenshaw et al. |
| 2010/0310628 A1 | 12/2010 | Waldburg-Zeil |
| 2011/0022171 A1 | 1/2011 | Richter et al. |
| 2011/0035004 A1 | 2/2011 | Maxwell |
| 2011/0054604 A1 | 3/2011 | Becker |
| 2011/0054605 A1 | 3/2011 | Becker |
| 2011/0106249 A1 | 5/2011 | Becker |
| 2011/0167602 A1 | 7/2011 | Altman et al. |
| 2011/0184227 A1 | 7/2011 | Altman et al. |
| 2011/0276039 A1 | 11/2011 | Markman |
| 2011/0288568 A1* | 11/2011 | Capuzziello .......... A61F 2/0063 606/151 |
| 2012/0010728 A1 | 1/2012 | Sun et al. |
| 2012/0034191 A1 | 2/2012 | Maltheny |
| 2012/0040013 A1 | 2/2012 | Owens et al. |
| 2012/0053690 A1 | 3/2012 | Frank |
| 2012/0059411 A1 | 3/2012 | Sun et al. |
| 2012/0061004 A1 | 3/2012 | Towler |
| 2012/0065649 A1* | 3/2012 | Towler ................ A61F 2/0045 606/151 |
| 2012/0158134 A1 | 6/2012 | Codori-Hurff et al. |
| 2012/0221105 A1 | 8/2012 | Altman et al. |
| 2012/0226352 A1 | 9/2012 | Becker et al. |
| 2012/0263763 A1 | 10/2012 | Sun et al. |
| 2012/0265218 A1 | 10/2012 | Chen et al. |
| 2012/0276213 A1 | 11/2012 | Chen |
| 2012/0283826 A1 | 11/2012 | Moses et al. |
| 2012/0310367 A1 | 12/2012 | Connor |
| 2012/0329034 A1 | 12/2012 | Chun et al. |
| 2013/0013068 A1 | 1/2013 | Forsell et al. |
| 2013/0103061 A1 | 4/2013 | Harper |
| 2013/0121970 A1 | 5/2013 | Owens et al. |
| 2013/0144356 A1 | 6/2013 | Horn et al. |
| 2013/0156744 A1 | 6/2013 | Taylor et al. |
| 2013/0158658 A1 | 6/2013 | Hayzlett |
| 2013/0211519 A1* | 8/2013 | Dempsey ................ A61F 2/12 623/8 |
| 2013/0224260 A1 | 8/2013 | Ward et al. |
| 2013/0287741 A1 | 10/2013 | Stillwell et al. |
| 2013/0317610 A1 | 11/2013 | Ledegerber |
| 2014/0081397 A1 | 3/2014 | Kalus |
| 2014/0100656 A1 | 4/2014 | Namnoum et al. |
| 2014/0257481 A1 | 9/2014 | Brooke et al. |
| 2014/0257482 A1 | 9/2014 | Ward et al. |
| 2014/0276957 A1 | 9/2014 | Locarno |
| 2014/0296623 A1 | 10/2014 | Owens et al. |
| 2014/0335144 A1 | 11/2014 | Ward et al. |
| 2015/0012089 A1 | 1/2015 | Shetty et al. |
| 2015/0037436 A1 | 2/2015 | Huang et al. |
| 2015/0150674 A1 | 6/2015 | Ansorge et al. |
| 2015/0157451 A1 | 6/2015 | Bowley et al. |
| 2015/0159066 A1 | 6/2015 | Hartwell |
| 2015/0209128 A1 | 7/2015 | Markman |
| 2015/0223928 A1 | 8/2015 | Limem |
| 2015/0250582 A1 | 9/2015 | Greenhalgh |
| 2015/0297798 A1 | 10/2015 | Badylak et al. |
| 2015/0320911 A1 | 11/2015 | Sun et al. |
| 2015/0351891 A1 | 12/2015 | Moses et al. |
| 2016/0000970 A1 | 1/2016 | Rosines |
| 2016/0022416 A1 | 1/2016 | Felix et al. |
| 2016/0030487 A1 | 2/2016 | Bachrach et al. |
| 2016/0030636 A1 | 2/2016 | Muir |
| 2016/0045198 A1 | 2/2016 | Bachrach |
| 2016/0135940 A1 | 5/2016 | Roock et al. |
| 2016/0151062 A1 | 6/2016 | Bachrach |
| 2016/0199173 A1* | 7/2016 | Liu ..................... A61L 27/3641 623/8 |
| 2016/0256259 A1 | 9/2016 | Wirth et al. |
| 2016/0256606 A1 | 9/2016 | Sun et al. |
| 2016/0262835 A1 | 9/2016 | Davila et al. |
| 2016/0271295 A1 | 9/2016 | Sun et al. |
| 2016/0287747 A1 | 10/2016 | Schallenberger |
| 2016/0331504 A1 | 11/2016 | Wang et al. |
| 2017/0007394 A1 | 1/2017 | Shetty et al. |
| 2017/0021058 A1 | 1/2017 | Huang et al. |
| 2017/0049549 A1 | 2/2017 | Bayat et al. |
| 2017/0049929 A1 | 2/2017 | Xu et al. |
| 2017/0049932 A1 | 2/2017 | Badylak et al. |
| 2017/0065742 A1 | 3/2017 | Sun et al. |
| 2017/0071725 A1 | 3/2017 | Barere et al. |
| 2017/0072110 A1 | 3/2017 | Ringo |
| 2017/0143475 A1 | 3/2017 | Moses et al. |
| 2017/0100509 A1 | 4/2017 | Sun et al. |
| 2017/0189165 A1* | 7/2017 | Hristov ................. A61B 8/481 |
| 2017/0202661 A1 | 7/2017 | Griffin et al. |
| 2017/0209619 A1 | 7/2017 | Monteiro et al. |
| 2017/0216008 A1 | 8/2017 | Markman |
| 2017/0216009 A1* | 8/2017 | Felix ..................... A61L 27/50 |
| 2017/0224460 A1 | 8/2017 | Ringo |
| 2017/0224869 A1 | 8/2017 | Shah et al. |
| 2017/0231753 A1 | 8/2017 | Lee |
| 2017/0281333 A1 | 10/2017 | Locarno et al. |
| 2017/0340437 A1* | 11/2017 | Bowley ................... A61F 2/12 |
| 2017/0348088 A1* | 12/2017 | Bunce .................... A61F 2/105 |
| 2017/0348353 A1 | 12/2017 | Sun |
| 2017/0348460 A1 | 12/2017 | Fang et al. |
| 2017/0367807 A1 | 12/2017 | Chen et al. |
| 2018/0008745 A1 | 1/2018 | Park et al. |
| 2018/0044629 A1 | 2/2018 | Qin et al. |
| 2018/0055624 A1 | 3/2018 | Barere et al. |
| 2018/0092737 A1 | 4/2018 | Barere et al. |
| 2018/0110612 A1 | 4/2018 | Schuessler et al. |
| 2018/0214262 A1 | 8/2018 | Diaz et al. |
| 2018/0214607 A1 | 8/2018 | Chen |
| 2018/0216062 A1 | 8/2018 | Chen et al. |
| 2018/0221136 A1* | 8/2018 | Kaplan .................. A61F 2/12 |
| 2018/0264037 A1 | 9/2018 | Owens et al. |
| 2018/0280132 A1 | 10/2018 | Shetty et al. |
| 2018/0333252 A1 | 11/2018 | Ansorge et al. |
| 2020/0054429 A1* | 2/2020 | Towfigh ............... A61F 2/0063 |
| 2020/0078165 A1 | 3/2020 | Spiegel |

FOREIGN PATENT DOCUMENTS

| | | |
|---|---|---|
| EP | 2692363 | 2/2014 |
| EP | 2692364 | 2/2014 |
| EP | 2926840 | 10/2015 |
| EP | 3034038 | 6/2016 |
| EP | 3056167 | 8/2016 |
| EP | 3056168 | 8/2016 |
| FR | 2746298 | 9/1997 |
| WO | 1984/004880 | 12/1984 |
| WO | 1999/065470 | 12/1999 |
| WO | 2005/063314 | 7/2005 |
| WO | 2008/066883 | 6/2008 |
| WO | 2008/148026 | 12/2008 |
| WO | 2008/154623 | 12/2008 |
| WO | 2009/065013 | 5/2009 |
| WO | 2010/027613 | 8/2009 |
| WO | 2010/071624 | 6/2010 |
| WO | 2011/011394 | 1/2011 |
| WO | 2011/019361 | 2/2011 |
| WO | 2012/031162 | 3/2012 |
| WO | 2009/065013 | 4/2013 |
| WO | 2013/106556 | 7/2013 |
| WO | 2013/126062 | 8/2013 |
| WO | 2013/137664 | 9/2013 |
| WO | 2013/192197 | 12/2013 |
| WO | 2014/008184 | 1/2014 |
| WO | 2014/019672 | 2/2014 |
| WO | 2014/047234 | 3/2014 |
| WO | 2014/145462 | 9/2014 |

(56) References Cited

FOREIGN PATENT DOCUMENTS

| WO | 2014/160008 | 10/2014 |
|---|---|---|
| WO | 2014/160124 | 10/2014 |
| WO | 2015/021807 | 2/2015 |
| WO | 2015/065923 | 5/2015 |
| WO | 2015/121686 | 8/2015 |
| WO | 2015/164728 | 10/2015 |
| WO | 2015/176014 | 11/2015 |
| WO | 2016/130559 | 8/2016 |
| WO | 2016/144475 | 9/2016 |
| WO | 2015/148932 | 10/2018 |
| WO | 2018/195476 | 8/2019 |
| WO | 2019/157048 | 8/2019 |

OTHER PUBLICATIONS

Butler et al. Reduction of Adhesions with Composite AlloDerm/Polypropylene Mesh Implants for Abdominal Wall Reconstruction. Plast. Reconstr. Surg.{2004), v114, p. 464-473.
Erdag, et al., "Fibroblasts Improve Performance of Cultured Composite Skin Substitutes on Athymic Mice", Burns, 30 {2004) pp. 322-328.
Final Office Action for U.S. Appl. No. 15/173,286, dated Jan. 26, 2018.
Final Office Action for U.S. Appl. No. 15/621,602, dated Nov. 13, 2017.
Final Office for U.S. Appl. No. 15/621,602, filed Jul. 12, 2018.
Further Examination Report in related New Zealand Patent Application No. 710330, dated Feb. 8, 2017.
Further Examination Report in related New Zealand Patent Application No. 710330, dated Oct. 11, 2016.
International Preliminary Report on Patentability for PCT/US2014/025619, dated Sep. 15, 2015.
International Search Report and Written Opinion for related International {PCT) Application No. PCT/US2014/025619, dated Jun. 30, 2014.
Isch et al., Patch Esophagoplasty Using AlloDerm as a Tissue Scaffold.Journal of Pediatric Surgery (2001 ), v36(2), pp. 266-268.
Kesmarky G., et al., "Plasma viscosity: A forgotten variable", Clinical Hemorcheology and Microcirculation, 2008, vol. 39, pp. 243-246, IOS Press.
Kolker et al., Multilayer Reconstruction of AbdominalWall Defects With Acellular DermalAllograft (AlloDerm) and Component Separation,Annals of Plastic Surgery (2005),v55(1), pp. 36-42.
Leung et al., Skin Grafts, UTMJ (2009), v86(2), pp. 61-64.
Li Y., et al., "Experimental validation of non-invasive and fluid density independent methods for the determination of local wave speed and arrival time of reflected wave", Journal of Biomechanics, 2011, vol. 44, pp. 1393-1399, Elsevier.
Mine et al. Aging Alters Functionally Human Dermal Papillary Fibroblasts but Not Reticular Fibroblasts: A New View of Skin Morphogenesis and Aging. PLoS One (2008), v3(12), e4066, 13 pages.
Mulder G. D., "Quantifying wound fluids for the clinician and researcher", Ostomy / Wound Management, 1994, vol. 40, pp. 65-69.
New Zealand Intellectual Property Office, First Examination Report in Applicant's related New Zealand Patent application No. 710330, dated Feb. 25, 2016 (4 pages).
Office Action for U.S. Appl. No. 151173,286, dated Aug. 3, 2017.
Office Action for U.S. Appl. No. 15/173,286, dated Jul. 10, 2018.
Office Action for U.S. Appl. No. 15/858,360 dated May 11, 2018.
Office Action in related Canadian Patent Application No. 2,899,642, dated Oct. 24, 2017.
Office Action in related Canadian Patent Application No. 2,899,642, dated Sep. 13, 2016.
Office Action issued for related European Patent Application No. 147182505, dated Nov. 23, 2016.
Oliver, et al., "Reconstruction of Full-Thickness Loss Skin Wounds Using Skin Collagen Allografts", British Journal of Plastic Surgery, 32 (1979), pp. 87-90.
Ownby, "The Integument—the skin and all of it's derivatives".
Patent Examination Report No. 1 in related Australian Patent Application No. 2014244272, dated Mar. 10, 2016.
Patent Examination Report No. 1 in related Australian Patent Application No. 2016234904, dated Apr. 28, 2017.
Restriction Requirement for U.S. Appl. No. 14/208,025, dated Nov. 3, 2015.
U.S. Appl. No. 14/208,025, filed Mar. 13, 2014.
U.S. Appl. No. 15/621,602, filed Jun. 13, 2017.
U.S. Appl. No. 15/915,412, filed Mar. 8, 2018.
U.S. Appl. No. 29/566,994, filed Jun. 3, 2016.
U.S. Appl. No. 15/032,567, filed Apr. 27, 2016.
U.S. Appl. No. 15/173,286, filed Jun. 3, 2016.
U.S. Appl. No. 15/858,360, filed Dec. 29, 2017.
U.S. Appl. No. 62/440,526, filed Dec. 30, 2016.
Final Office Action for U.S. Appl. No. 14/208,205, dated Aug. 19, 2016.
Office Action for U.S. Appl. No. 14/208,025, dated Feb. 26, 2016.
Office Action for U.S. Appl. No. 14/208,025, dated Mar. 13, 2017.
Office Action for U.S. Appl. No. 15/621,602, dated Jul. 12, 2018.
Office Action for U.S. Appl. No. 15/621,602, dated Aug. 10, 2017.
Shuster et al. The influence of age and sex on skin thickness, skin collagen and density. British Journal of Dermatolog 1975), v96, p. 639-643.
U.S. Appl. No. 61/783,237, filed Mar. 14, 2013.
U.S. Appl. No. 62/468,511, filed Mar. 8, 2017.
U.S. Appl. No. 29/662,750, filed Sep. 7, 2018.
Australian Patent Application No. 2019204393, filed on Jun. 21, 2019.
Canadian Design Application No. 186423, filed on Mar. 7, 2019.
Canadian Patent Application No. 3053144, filed on Aug. 27, 2019.
European Design Application No. 006280178, filed on Mar. 5, 2019.
European Patent Application No. 19190980.3, filed on Aug. 9, 2019.
Partial European Search Report for EP Patent Application No. 19190980.3 dated Feb. 17, 2020.
Examination Report from corresponding Canadian Design Application No. 186423, dated Feb. 12, 2020.
Final Office Action for U.S. Appl. No. 15/173,286, dated Nov. 25, 2019.
Notice of Allowance for U.S. Appl. No. 29/662,750.
Office Action from corresponding Canadian Patent Application No. 3,053,144, dated Sep. 1, 2020.

* cited by examiner

SOFT TISSUE REPAIR GRAFTS AND PROCESSES FOR PREPARING AND USING SAME

FIELD OF THE INVENTION

The present invention relates generally to grafts for soft tissue repair and capable of supporting, covering or retaining an implant positioned in the body of a subject. More particularly, the present invention relates to grafts capable of supporting, covering and retaining an implant for breast reconstruction and similar plastic surgery procedures, and especially for pre-pectoral breast reconstruction procedures.

BACKGROUND OF THE INVENTION

Surgical procedures for the repair, reconstruction and modification of tissues, organs, and other body parts of humans and other species are common. Such surgical procedures include, for example, the repair of ventral abdominal hernias and other abdominal wall defects, the repair and reconstruction of bone and skin having damage from injury or disease, and the reconstruction or modification of the breast, nose, buttocks and other organs and body parts to repair damage from injury or disease or for aesthetic reasons.

These repair, reconstruction and modification procedures often involve the use of grafts which serve to replace, restore or supplement the structure or function of the tissues, organs, or other body parts being treated. In some cases, grafts are used to support, cover and/or retain one or more other devices (e.g., an implant), to achieve the desired repair and reconstruction. Grafts may also be used to deliver and administer therapeutic agents or substances, such as pharmaceutical compounds, antibiotics, tissuegenic agents, bioactive substances, etc.

Grafts must generally be biocompatible and not immunogenic. In addition, depending on the particular surgical procedure, differences in the size, shape, flexibility, density, tensile strength, ability to retain or release therapeutic agents or substances, ability to support and grow cells, and other properties, may be beneficial. For example, materials initially having a generally planar or sheet-like configuration, with good flexibility and tensile strength, have been found useful for making grafts to support and retain a breast implant such as that implanted during breast reconstruction.

Breast reconstruction procedures are sometimes performed to repair and reconstruct a breast from which tissue has been removed, such as by mastectomy to remove cancerous tissue, in which case a breast implant substitutes for the removed tissue. Sometimes breast reconstruction is performed for breast augmentation and the breast implant adds volume to existing tissue. In any case, the breast implant should enable formation of a natural breast shape.

Materials used to make grafts for breast reconstruction should possess biomechanical properties including predictable suppleness, flexibility and uniform pliability sufficient for such grafts to stretch and expand without tearing during tissue expansion (i.e., using the breast implant and/or a tissue expander), as well as to conform to both the shape and contour of the implant and the shape and contour of the breast pocket. The most suitable materials for breast reconstruction and similar plastic surgery procedures should also possess sufficient tensile strength to preclude suture tear-out, both during implantation and expansion through the post-operative phase, and allow rapid and efficient cellular ingrowth equally from either side of the graft.

For example, processed dermal tissue, which has been decellularized to reduce immunogenicity, is generally known to possess the aforesaid biomechanical properties and has been used in breast reconstruction procedures with some success as grafts for covering, supporting, and/or retaining breast implants. Such acellular dermal matrices ("ADMs") are commercially available, including FlexHD Structural® ADM and FlexHD Pliable® ADM, both of which are marketed by Musculoskeletal Transplant Foundation (Edison, N.J.), as well as AlloDerm® ADM and AlloDerm® Ready to Use ("RTU") ADM, both of which are marketed by LifeCell Corporation (Branchburg, N.J.). The ADMs are cut to suitable dimensions and shape to conform to the breast implant and the implant location in the patient. Furthermore, while suitable ADM may be derived from almost any animal having skin, ADMs used for breast reconstruction procedures have most often been derived from mammals, and especially humans and pigs.

Historically, the first breast reconstruction procedures were performed with a breast implant simply placed in a breast pocket, such as created by mastectomy, to replace the excised breast tissue. Unfortunately, this method was fraught with problems, mainly related to capsular contracture, with resulting hardening of the implants and externally visible rippling or puckering of the skin and underlying tissue. This capsular contracture was found to be reduced when muscle coverage is added over the implant. Therefore, to overcome the capsular contracture problem, the breast implants were then placed under (i.e., behind) the chest muscles, i.e., the pectoralis major and serratus anterior. This, however, resulted in other complications, including a much less natural shape for the reconstructed breast (due to muscle forces over the implant) and significantly more discomfort for the patient.

To address the foregoing issues, grafts made from ADM were developed and positioned to support the breast implant inferiorly (i.e., from underneath), which allowed the implant to still be placed under the pectoralis major. It has been shown that use of grafts made of ADM for breast reconstruction with breast implants decreased capsular contracture.

A more recently developed technique, known as pre-pectoral breast reconstruction, involves placement of the breast implant in front of the patient's chest muscles (i.e., pectoralis major), with total anterior coverage of the breast implant by an ADM graft instead. Such pre-pectoral ADM grafts have been cut from an ADM, at the time of the reconstruction procedure, to a size and shape suitable to cover the anterior of the breast implant and thereby support the breast implant without the need of pectoralis muscle. The ADM graft extends around the breast implant and is sutured to the pectoralis major at its peripheral edge to form a three-dimensional structure within which the breast implant is held. Thus, the shape of the ADM graft is important for achieving close conformance between the ADM graft, implant and surrounding tissue to reduce patient discomfort and aesthetically undesirable rippling or puckering. This arrangement provides improved results over the technique of placing the breast implant beneath the chest muscle, including a more natural shape for the reconstructed breast and reducing post-operative patient discomfort, while still minimizing capsular contracture and the complications caused thereby.

Nonetheless, further improvements to the results achieved by pre-pectoral breast reconstruction are desired, including more precise positioning of the graft with relation to the nipple, overall breast configuration and breast implant, as well as minimizing post-operative suture tear out, capsular contracture and development of externally visible rippling and other aesthetically unattractive, or physically painful and/or uncomfortable post-operative features. Accordingly, design modifications to grafts used to cover and support the breast implants in pre-pectoral breast reconstruction procedures, regardless of whether the grafts are made of ADM, have been developed that address the foregoing issues.

SUMMARY OF THE INVENTION

The present invention relates to a graft for soft tissue repair, and more particularly to a graft configured for use in pre-pectoral breast reconstruction surgical procedures.

BRIEF DESCRIPTION OF THE DRAWINGS

The present invention will be further explained with reference to the attached drawings, wherein like structures are referred to by like numerals and/or letters throughout the several views. The drawings shown are not necessarily to scale, with emphasis instead generally being placed upon illustrating the principles of the present invention.

DETAILED DESCRIPTION OF THE INVENTION

Figure 1:
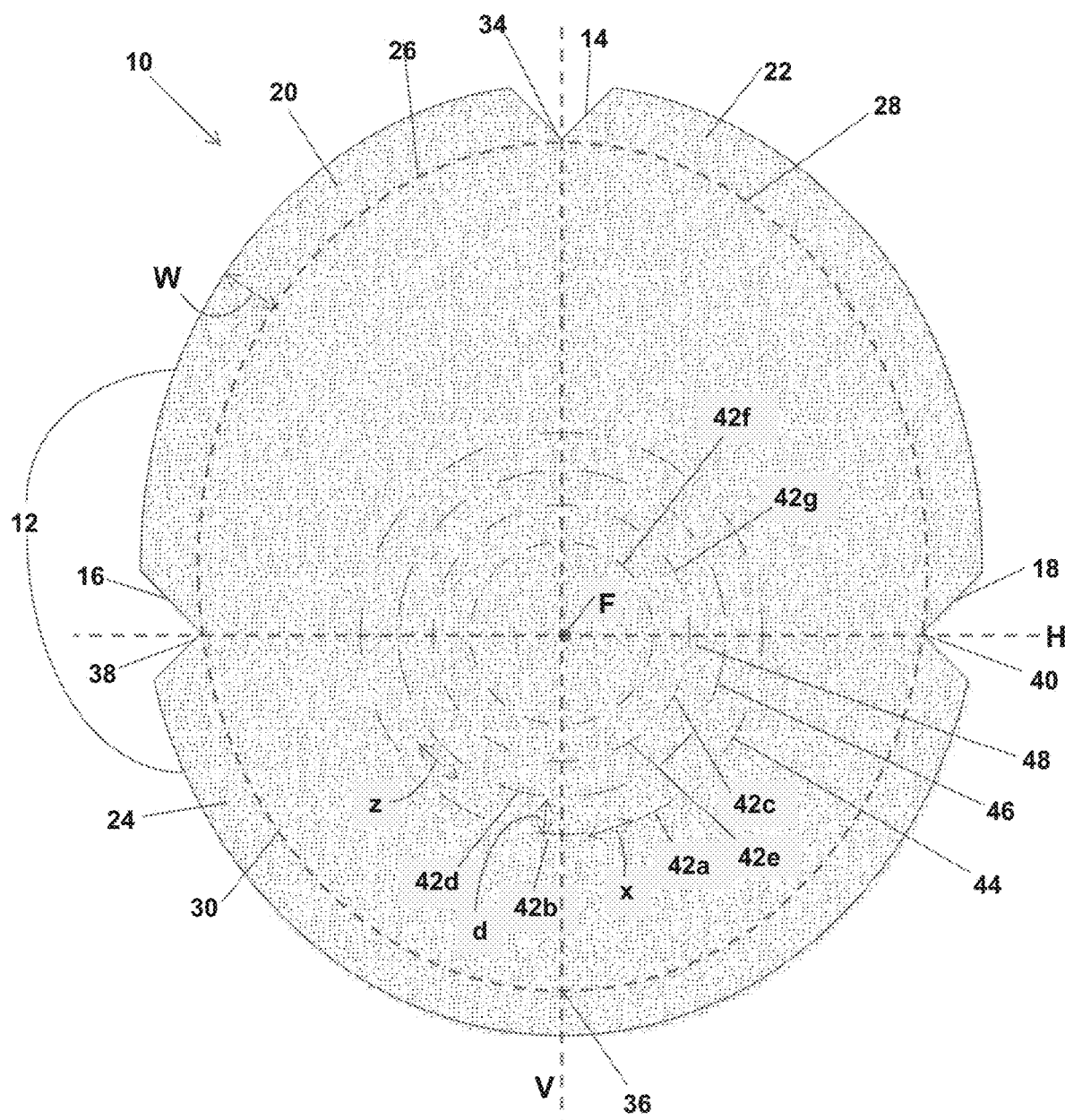
FIG. 1 is a top plan view of an exemplary embodiment of a soft tissue repair graft.

Detailed embodiments of the present invention are disclosed herein. It should be understood that the disclosed embodiments are merely illustrative of the invention which may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The term "graft" refers to a biologically compatible material, tissue, or substance which is introduced into the body of a subject, either permanently or temporarily, to replace, improve or supplement the structure or function of tissue, an organ, or other body feature of the subject and includes, but is not limited to, those used for the administration or delivery of a therapeutic agent or substance. In the case of the grafts described herein which are used in pre-pectoral breast reconstruction procedures, planar grafts are generally most suitable, however, the term "graft" as used herein is not limited only to those having planar configurations. Grafts may be integrated into a patient's body after implantation.

Where a graft is made of material obtained from the same individual into whom it is implanted, it is "autologous." Where the graft is made of material obtained from a different individual of the same species than the individual into whom it is implanted, it is "allogeneic." Where the graft is made of material obtained from an individual of a different species than the individual into whom it is implanted, it is "xenogeneic." The soft tissue grafts may be autologous, allogeneic or xenogeneic.

The term "implant" means a device or material that replaces a missing body feature or portion thereof, which may be lost through trauma, disease, or congenital conditions, and is intended to restore the normal function(s) of the missing body part. Furthermore, an implant can be any material, device or substance which is introduced into the body of a subject, either permanently or temporarily, to replace, improve or supplement the structure or function of tissue, an organ, or other body feature of the subject and includes, but is not limited to, those used for the administration or delivery of a therapeutic agent or substance.

The term "biocompatible" means that the graft or implant, when implanted in a subject, does not cause adverse effects such as, for example without limitation, toxicity, foreign body reaction, or cellular disruption.

Grafts for soft tissue repair described herein are suitable for supporting, covering, retaining, or any combination thereof, an implant positioned in the body of a subject. More particularly, the soft tissue repair grafts are capable of being more accurately positioned in a subject and more securely attached to adjacent tissues than previously known grafts. Furthermore, the soft tissue repair grafts are capable of greater expansion without tearing during tissue expansion (i.e., using breast implant and/or tissue expander), while concurrently conforming more closely to the shapes and contours of both the implant and adjacent body tissues, than previously known grafts. The improved ability of the soft tissue graft to conform closely to the shapes and contours of the implant and adjacent body tissues is more significant and apparent when those contours are more rounded, curved, protruding, or recessed (e.g., concave, convex, projecting, etc.), such as, without limitation, for a breast, knee joint, elbow joint, chin, fingertip, toe, heel, other similar body features, and implants for such body features.

While the aforesaid soft tissue grafts will be described in detail hereinafter as used in surgical procedures for breast reconstruction, their utility is not limited to such surgical procedures. Rather, persons of ordinary skill will recognize that the soft tissue grafts are advantageous for other surgical procedures as well, particularly those involving repair, reconstruction or modification of body features such as those mentioned above and others.

The features of the soft tissue repair grafts that provide the aforesaid improved characteristics will now be discussed with reference to FIGS. 1-2C. More particularly, FIG. 1 is a top plan view of an exemplary soft tissue repair graft 10 suitable for use in a surgical procedure such as breast reconstruction. The soft tissue repair graft 10 has an arcuate peripheral edge 12 and a focal point F which is located generally at or near the geometric center of the graft 10. An imaginary vertical axis V passes through the focal point F. An imaginary horizontal axis H also passes through the focal point F, with the vertical and horizontal axes V, H intersecting at the focal point F. In embodiments where the graft 10 is intended for use in pre-pectoral breast reconstruction procedures, for example, the focal point F will be positioned at the nipple of the breast undergoing reconstruction.

As shown in FIG. 1, the graft 10 has a generally circular or slightly oval shape. As will be understood by persons of ordinary skill in the relevant art, the graft 10 will have dimensions suitable for the location and size of the surgical site with which it is intended for use. For example, a larger sized graft 10 will be suitable and selected for a larger sized breast or breast pocket, and a smaller sized graft 10 will be suitable and selected for a smaller breast size. Generally, when the graft 10 has a generally oval shape and is intended for use in a breast reconstruction procedure, the vertical axis V will be of greater length than the horizontal axis H. More particularly, in some embodiments of grafts for use in pre-pectoral breast reconstruction, the ratio of the length ($L_v$) of the vertical axis V to the length ($L_H$) of the horizontal axis H may be from about 1.05 to about 1.30, such as from about 1.10 to about 1.20, or about 1.15.

Additionally, as shown in FIG. 1 and for purposes described hereinafter, the graft 10 has at least three notches 14, 16, 18 at the peripheral edge 12, including a top notch 14 located where the vertical axis V meets the peripheral edge 12 above the focal point F, and first and second side notches 16, 18 located where the vertical axis V meets the peripheral edge 12 on opposite sides of the focal point F. In embodiments of the graft 10 having three notches 14, 16, 18, as shown in FIG. 1, for example, a user (e.g., surgeon) handling the graft 10 prior to implantation in a subject will be able to readily discern which is the top notch 14 and, therefore, which way to orient the graft 10 to ensure it is positioned properly to align with the shape and anatomy of the breast or breast pocket being reconstructed. More particularly, when the graft 10 has three notches 14, 16, 18 as described above and shown in FIG. 1, a user may determine a sequence of the notches 14, 16, 18 which extends the shortest overall distance and the notch 14 positioned in the middle of the other two 16, 18 is the top notch 14.

With reference still to FIG. 1, due to the presence of the notches 14, 16, 18, the peripheral edge 12 is discontinuous and a plurality of cuff elements 20, 22, 24 are formed. Each cuff element 20, 22, 24 is foldable along a respective imaginary arcuate line 26, 28, 30 (see dotted lines in FIG. 1) which extends from the base of a respective pair of notches which forms each cuff element 20, 22, 24 to form a folded edge (see folded edge 32 shown in FIG. 2C). For example, with reference to FIG. 1, one cuff element 20 is foldable along its respective imaginary arcuate line 26 between the notches 14, 16 which form that cuff element 20. When all cuff elements 20, 22, 24 are thus folded, a reinforced folded edge 32 (see FIG. 2C) extends substantially around the entire graft 10. When thus folded, the cuff elements provide a superior ring (i.e., the reinforced folded edge 32) of contact with the muscle M for improved long term support of the implant I (see, particularly, FIGS. 2B and 2C). Each cuff element 20, 22, 24 may, for example without limitation, have a width W, measured from the peripheral edge 12 of the graft 10 (see FIG. 1), of from about 7 millimeters to about 20 millimeters. In some embodiments, each cuff element 20, 22, 24 has a width of from about 10 millimeters to about 20 millimeters, or from about 15 millimeters to about 20 millimeters, or from about 10 millimeters to about 15 millimeters, or even from about 12 millimeters to about 18 millimeters. The width of each cuff element 20, 22, 24 will typically be based on the size of the breast implant being used, as is readily determinable by persons of ordinary skill in the relevant art. It should be further noted that where the graft 10 has more than one cuff element, they need not all have the same widths as one another.

In some embodiments (not shown per se), the graft 10 may be symmetrical, such that the vertical and horizontal axes V, H each extend to the farthest and oppositely positioned points on the reinforced folded edge 32 and are substantially perpendicular with one another. In other embodiments such as that shown in FIG. 1, the graft 10 may be symmetrical only along the vertical axis V, such that the vertical and horizontal axes V, H each extend to the farthest and oppositely positioned points 34, 36, 38, 40, respectively, on the folded edge 32 and are perpendicular with one another, but the focal point F is a shorter distance from a bottommost (i.e., inferior) point 36 than from a topmost (i.e., superior) point 34 on the folded edge 32. In some embodiments of the graft 10 suitable for use in pre-pectoral breast reconstruction procedures, the distance between focal point F and the bottommost point 36 is from about 40% to about 50%, such as from about 42% to about 48%, or such as about 45%, of the total distance between the topmost point 34 and the bottommost point 36, thus optimizing distribution of breast volume around the nipple for improved breast shape and aesthetic outcome. In still other embodiments (not shown), the graft 10 may be asymmetrical, such that the vertical and horizontal axes V, H each extend to the farthest and oppositely positioned points on the folded edge 32, but are not perpendicular with one another. Embodiments of the graft 10 which are either symmetrical only about the vertical axis V or asymmetrical may align more closely with a breast and, therefore, may be more suitable for use in breast reconstruction procedures. In all embodiments, the focal point F will be located at the intersection of the vertical axis V and horizontal axis H. In fully or partially symmetrical embodiments of the graft 10 described above, the focal point F is also positioned at the midpoint of the horizontal axis H.

Although not shown in the figures, as will be recognized by persons of ordinary skill in the relevant art, the graft 10 may have different quantities of notches and cuff elements. For example without limitation, in some embodiments the graft 10 may not have any notches, in which case the cuff element may also be entirely absent. Alternatively, as will be described below, in some embodiments of the graft 10 which lack any notches, there may be a single cuff element which extends at least partially, or even entirely, around the periphery of the graft 10 for folding to form a reinforced edge which would be coextensive with the single cuff element. Furthermore, as will also be understood by persons of ordinary skill in the relevant art, the graft 10 may, for example without limitation, include only two notches or even a single notch (such as, but not necessarily, positioned at the topmost (i.e., superior) point 34 of the graft 10), which could form two cuff elements (by two notches), or a single cuff element or even no cuff element at all (by a single notch). For example, a graft might include one or more notches which are too shallow or small to form cuff elements wide enough to be used and beneficial in the manner described above, but the notches would still perform the function of providing guidance for properly orienting the graft during its placement in a breast undergoing reconstruction. Thus, it is possible to produce the respective benefits of the notches or the cuff elements separately, i.e., even in the absence of the other feature. All such embodiments are within the scope of the grafts contemplated and described herein. The configuration of three notches 14, 16, 18 and three cuff elements 20, 22, 24 shown in the figures and described in detail hereinabove provides an efficient and effective combination of these features to provide the positional guidance for orientation of the graft 10 by a surgeon during pre-pectoral breast reconstruction, as well as formation of the reinforced folded edge 32 for securing the graft 10 (and thereby, the implant I), such as with sutures, in the desired position within the reconstructed breast B.

The graft 10 may include a plurality of arcuate slots or openings 42a, 42b, 42c, 42d, 42e, 42f, 42g at least partially through the graft 10, which form a plurality of circular patterns 44, 46, 48 which are concentric about the focal point F. The concentric, circular pattern of slots or openings 42, 44, 46, 48 about focal point F allow for expansion of the two dimensional graft 10 to reshape into a three dimensional structure which conforms in least in part to the spherical shape of the breast implant. In some embodiments, at least some of the arcuate slots or openings 42a, 42b, 42c, 42d, 42e, 42f, 42g are entirely through the graft 10. In preferred embodiments of the graft 10, the slots or openings 42a, 42b, 42c, 42d, 42e, 42f, 42g are not mere holes or perforations, but rather, each of them 42a, 42b, 42c, 42d, 42e, 42f, 42g is elongated. The length of each individual slot (e.g., 42a, 42b, 42c, 42d, 42e, 42f, 42g), for example without limitation, is typically from about 5 millimeters and about 15 millimeters, with longer slots (e.g., slot 42a, 42b) forming the outer circular patterns (e.g., pattern 44) and shorter slots (e.g., slot 42e) forming inner circular patterns (e.g., pattern 48). Additionally, for example without limitation, in some embodiments, the distance x (see FIG. 1) between successive slots (end-to-end) (e.g., slots 42a, 42b) should be from about 5 millimeters to about 15 millimeters, such as about 10 millimeters.

Typically, the slots 42a, 42b forming the outermost circular pattern 44, are not closer than about 1.75 centimeters, such as without limitation, not closer than about 1.25 centimeter, or even about 1.5 centimeters, from the imaginary arcuate lines 26, 28, 30, between the notches 14, 16, 18 (or from the reinforced folded edge 32 of the graft 10 after implanting). This placement of the slots 42a, 42b of the outermost circular pattern 44 minimizes the risk of unnecessarily weakening the tensile strength of the graft 10 during and after implantation.

The distance d (see FIG. 1) between the slots (e.g., slots 42b, 42d) forming adjacent circular patterns (e.g., patterns 44, 46) should be from about 10 millimeters to about 20 millimeters, such as about 15 millimeters. In some exemplary embodiments, for larger sized grafts (such as having a largest diameter of from about 26 to about 22 centimeters, such as about 25 centimeters), the distance d between the slots (e.g., slots 42a, 42c) forming adjacent circular patterns (e.g., patterns 44, 46) should be from about 15 millimeters to about 20 millimeters. In some exemplary embodiments, for medium or average sized grafts (such as having a largest diameter of from about 24 to about 20 centimeters, such as about 22 centimeters), the distance d between the slots (e.g., slots 42a, 42c) forming adjacent circular patterns (e.g., patterns 44, 46) should be from about 13 millimeters to about 17 millimeters. In some exemplary embodiments, for smaller sized grafts (such as having a largest diameter of from about 18 to about 22 centimeters, such as about 20 centimeters), the distance d between the slots (e.g., slots 42a, 42c) forming adjacent circular patterns (e.g., patterns 44, 46) should be from about 10 millimeters to about 15 millimeters.

Figure 2A:
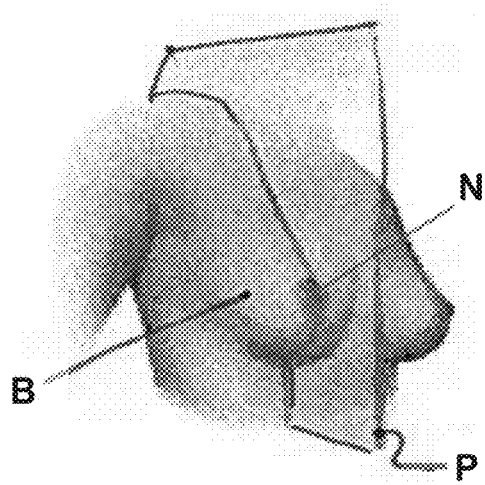
FIG. 2A is a perspective view of a subject having a breast to be reconstructed.
Figure 2B:
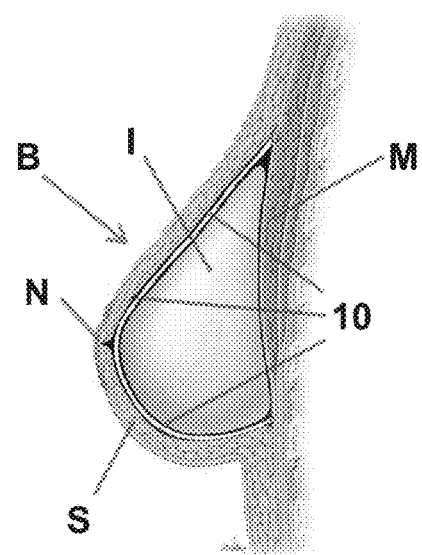
FIG. 2B is a cross-sectional side view of the subject of FIG. 2A, taken along the plane P, showing the breast B after reconstruction by a pre-pectoral reconstruction technique with a breast implant and a graft according to FIG. 1.
Figure 2C:
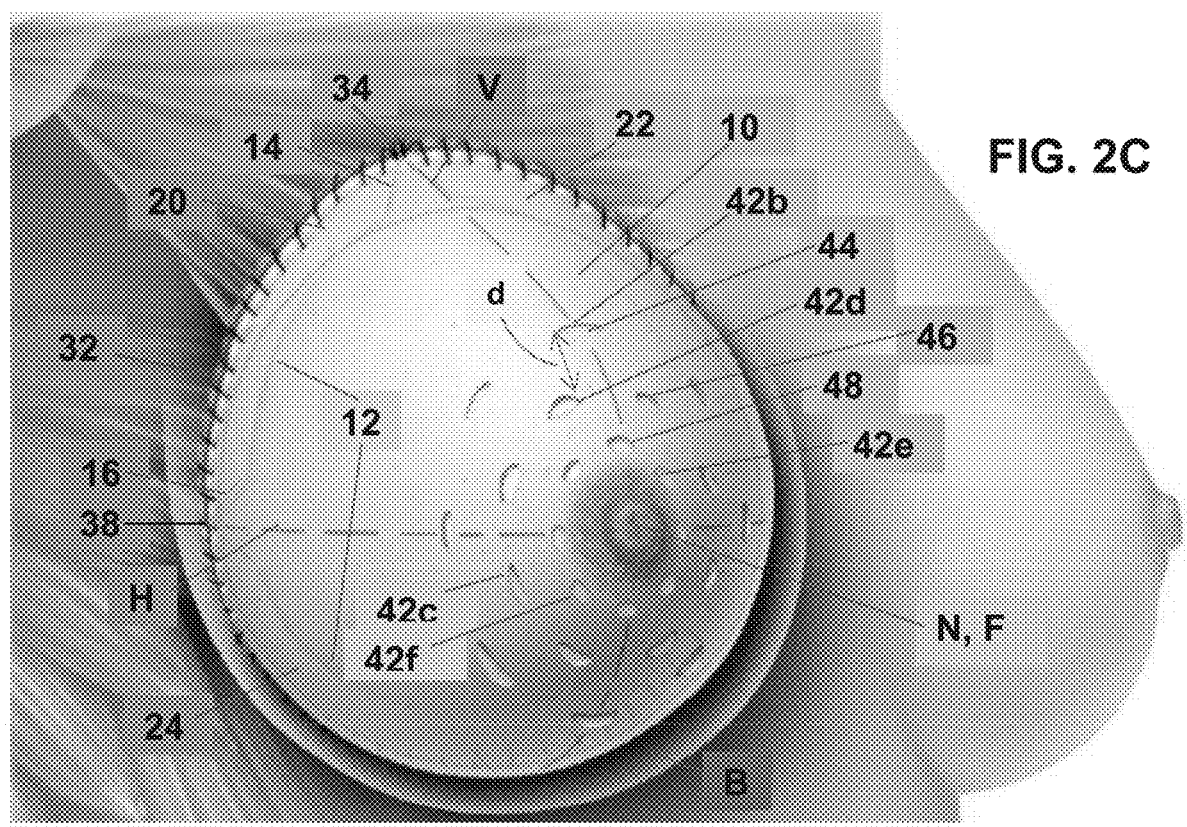
FIG. 2C is a perspective view of the subject and reconstructed breast of FIG. 2B, where the skin flap S has been removed to show the chest muscle and implanted graft.

With reference now to FIGS. 2A, 2B and 2C, the use of the soft tissue graft 10 in connection with pre-pectoral breast reconstruction, and the benefits provided by the aforesaid features, will now be described. Embodiments of the soft tissue graft 10 intended for use in breast reconstruction procedures are generally implanted such that they at least partially cover, support and retain a breast implant I within the breast B of a subject.

FIG. 2A shows a perspective view of a subject having a breast B to be reconstructed. FIG. 2B provides a cross-sectional side view of the subject of FIG. 2A, taken along the plane P, showing the breast B, after reconstruction using a pre-pectoral reconstruction technique to implant a breast implant I and an exemplary embodiment of the graft 10. In FIG. 2B, the chest muscle M as well as the skin flap S and nipple N of the breast B are shown, with the graft 10 positioned in front of the chest muscle M and adjacent to the skin flap S, and the breast implant I positioned in a pocket formed between the chest muscle and the graft 10.

One technique for performing pre-pectoral breast reconstruction, for example where a previous mastectomy procedure has already removed breast tissue and left a pocket between the breast muscle and skin, is to lift the skin flap S away from the chest muscle M of the breast, fold the cuff elements 20, 22, 24 of a graft 10 to form a reinforced folded edge 32 and insert the graft 10 superior to the chest muscle (pectoralis major) M and anterior and adjacent to the skin flap S of the breast B. The graft 10 is oriented and inserted in the pocket between the chest muscle M and skin flap S with its top notch 14 vertically aligned above the nipple N, and its focal point F directly underlying the nipple N. This cuff allows for some surface area of the graft that is folded under the implant to come in contact with the muscle and function as an anchor providing extra support for the graft-implant construct resulting in improved positioning of the implant long-term, thus counteracting forces of gravity long-term. Without the cuff, the graft-implant construct would only be in contact and supported by the breast skin, which stretches with time.

The graft 10 is affixed to the chest muscle M by suturing along almost the entire length of the reinforced folded edge 32 from the 4 o'clock position to the 8 o'clock position along the superior edge [26, 28, 30] and leaving a short portion (for example without limitation, from about 4.5 centimeters to about 8.5 centimeters in length) of the folded edge 32 unsutured so that a pocket (not shown per se) is formed between the chest muscle M and the graft 10. A breast implant I or other biocompatible medical device (e.g., tissue expander) is inserted into the pocket and the pocket is then closed by suturing the remaining short portion of the folded edge 32 of the graft 10 to the chest muscle M. Suture failure, sometimes referred to as suture "tear-out," often results in post-operative complications including, without limitation, the graft 10 and/or breast implant I shifting position relative to the natural breast B and nipple N, which may cause undesirable cosmetic changes and pain. The reinforced folded edge 32 formed by folding the cuff elements 20, 22, 24 of the graft 10 provides a location for suturing the graft 10 to the chest muscle M which reduces the risk of suture tear-out and corresponding complications.

Additionally, the reinforced folded edge 32 of the graft also provides an area for tissue ingrowth and stabilization of the pocket beyond sutures. As will be recognized by persons of ordinary skill in the relevant art, and although not specifically shown, even if the graft 10 does not include notches 14, 16, 18, a portion of the graph proximate the peripheral edge 12 may nonetheless be folded against the graft 10, in a single continuous cuff element, to form a reinforced folded edge 32 at which the graft 10 may be affixed to the chest muscle M with sutures (or staples, etc.), although there may be some slight puckering or gathering of the continuous cuff element portion of the peripheral edge 12. Thus, the notches 14, 16, 18 serve not only as orientation guides as described above, but also minimize puckering and gathering along the folded edge 32 of the graft 10.

FIG. 2C provides a perspective view of the subject and reconstructed breast B, where the skin flap S has been removed to render the chest muscle M and implanted graft 10 visible. FIG. 2C also shows the nipple N artificially superimposed on the graft 10 to show its location relative to the graft 10 and its plurality of slots 42a, 42b, 42c, 42d, 42e, 42f, 42g and circular patterns 44, 46, 48. The elongate and arcuate shape of the plurality of slots 42a, 42b, 42c, 42d, 42e, 42f, 42g enables the graft 10 to expand and stretch to a greater extent than if only holes or perforations were provided in the graft 10, which allows the graft 10 to cover and more closely conform to the shape and contours of the implant I while avoiding failure (i.e., tearing) of the graft 10 itself. The circular patterns 44, 46, 48 and concentric arrangement of the plurality of slots 42a, 42b, 42c, 42d, 42e, 42f, 42g around the focal point F further enable the graft 10 to conform more closely to the shapes and contours of both the breast implant I and the skin flap S and minimize post-operative complications such as rippling and puckering.

As already discussed above, the graft 10, as described and shown in the figures, may include a plurality of both notches 14, 16, 18 and cuff elements 20, 22, 24. However, the graft 10 may instead include one or more notches, or one or more or cuff elements, or one or more of both notches and cuff elements, and the quantities of notches and cuff elements need not be the same. Furthermore, the graft 10 may include a plurality of slots 42a, 42b, 42c, 42d, 42e, 42f, 42g which are arranged in a plurality of concentric circular patterns 44, 46, 48, as described above, regardless of whether or not the graft 10 includes also includes any notches, slots, or both. In some embodiments, for example without limitation, the graft 10 may include such a plurality of slots 42a, 42b, 42c, 42d, 42e, 42f, 42g, but not have any notches or cuff elements. Although these features may cooperate to provide a graft having multiple advantages and improved results as compared to other grafts without such features, as described above, each of these features provides advantages and improved results independently of the others.

Suitable materials for making the soft tissue grafts 10 described herein include various tissues such as, without limitation, amnion, chorion, dermal, duodenum, dura, fascia lata, gastrointestinal, intestinal mucosa, intestinal submucosa, pericardium, peritoneum, placenta, and umbilical cord. The most suitable materials for breast reconstruction and similar plastic surgery procedures will possess sufficient tensile strength to minimize or avoid suture tear-out, both during implantation and expansion through the post-operative phase, and allow rapid and efficient cellular ingrowth equally from either side of the graft.

While not the only particularly suitable material, acellular dermal matrices (ADMs) have been known and used to make grafts for soft tissue repair procedures, including without limitation breast reconstruction and other cosmetic surgical procedures. Such materials are known to have suitable structural and biomechanical properties including, but not limited to, predictable suppleness, flexibility, uniform pliability sufficient to stretch and expand without tearing during tissue expansion (i.e., using a breast implant and/or tissue expander), and sufficient tensile strength.

Figure 3:
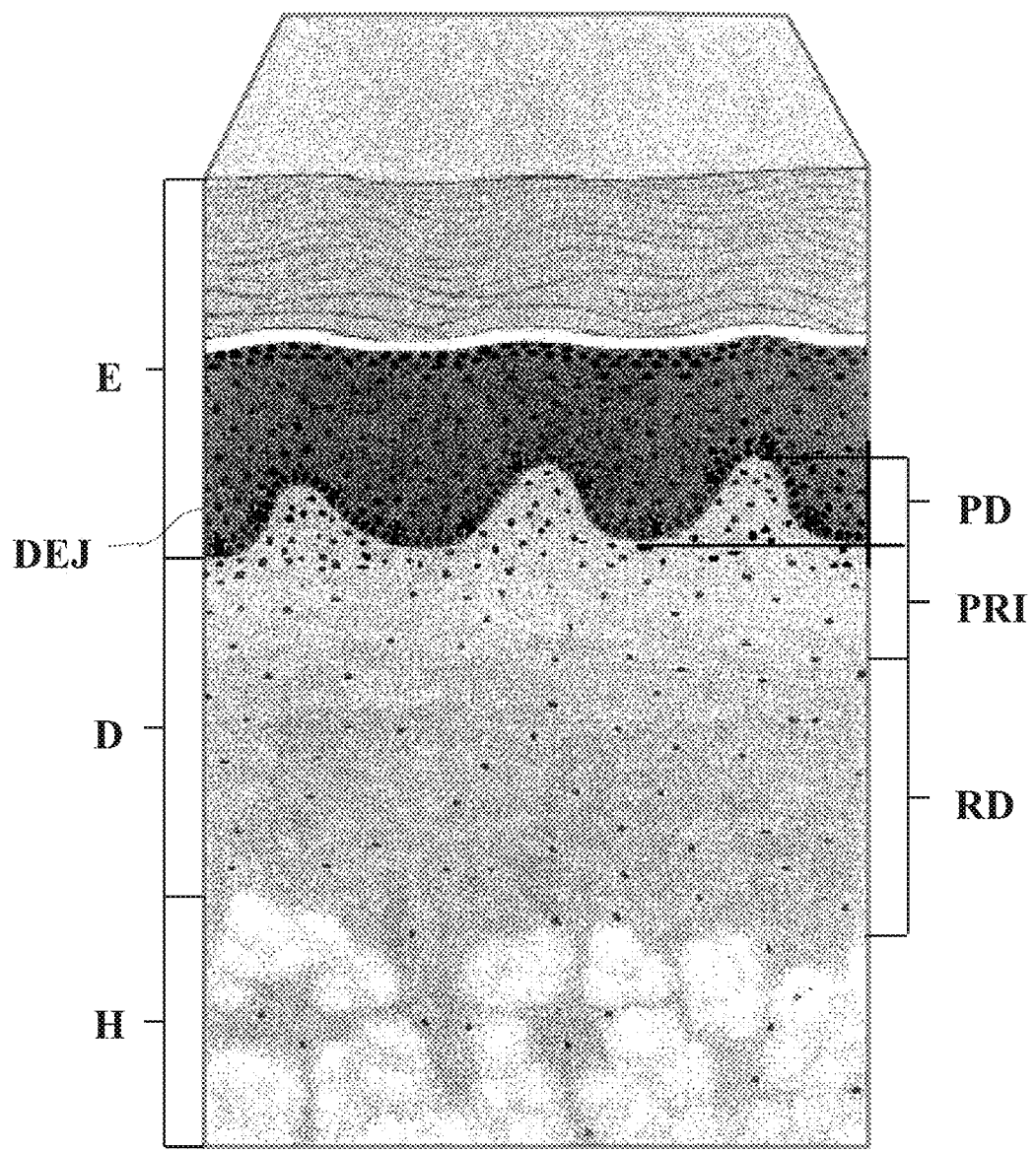
FIG. 3 is a perspective schematic view of a section of human skin and the various components thereof, from which acellular dermal matrices (ADMs) may be fabricated.

The nature of the dermal tissue from which these ADMs are derived is explained with reference to FIG. 3, which illustrates the microstructure of human skin. Human skin is recovered from either live or deceased donors after receiving consent from the individual donor or donor's family. As illustrated in FIG. 3, human skin is made of several layer-like components, including the outer-most epidermis E, and the dermis D, which lies beneath the epidermis. The hypodermis H (also referred to as the subcutis) lies beneath the dermis D, but is not part of the skin. Rather, the hypodermis H contains adipose and muscle tissue. The dermis D itself includes the papillary dermis PD, which lies adjacent the epidermis E, and the reticular dermis RD, which lies between the papillary dermis PD and the hypodermis H. The papillary-reticular dermis interface PM, lies between the papillary dermis PD and the reticular dermis RD. The dermis-epidermis junction ("the DEJ") lies between the papillary dermis PD and epidermis E.

The process for deriving the foregoing ADMs from dermal tissue involves removing the epidermis E (e.g., by a chemical process that causes the epidermis to slough off), and thereby exposing the DEJ that was adjacent the epidermis E. Beneath the DEJ lies the papillary dermis PD, the papillary-reticular dermal interface PM, and the reticular dermis RD. The dermal tissue that is recovered for the ADMs may therefore include the DEJ, papillary dermis PD and at least part of the reticular dermis RD. The recovered dermal tissue is decellularized and aseptically processed to meet sterility testing requirements.

The foregoing ADMs are derived from recovered tissue that includes the entire papillary dermis PD. The microstructure of the papillary dermis PD is not uniform. More particularly, the papillary dermis PD has an upper portion, or side, that was immediately adjacent the DEJ and therefore closer to the epidermis E (i.e., "the epidermal portion"), and a structurally different lower portion, or side, that was farther from the DEJ and epidermis E, and adjacent the deeper reticular dermis RD (i.e., "the dermal portion"). The epidermal portion of the papillary dermis PD contains a more densely-packed collagen matrix than the relatively more open collagen matrix contained in the dermal portion. As such, the dermal portion is more porous than the epidermal portion. This dual structure is also a property of the foregoing ADMs, and is ideal for repairing ventral abdominal hernias and other abdominal wall defects, as the more densely-packed epidermal portion of the ADM (i.e., incorporating the epidermal portion of the papillary dermis PD) possesses the tensile strength and stiffness required for such load-bearing tissue repairs, and the more porous dermal portion of the ADM (i.e., incorporating the dermal portion of the papillary dermis PD, as well as at least a portion of the loosely-packed and porous underlying reticular dermis RD) provides an open collagen structure that promotes vascularization, cellular attachment and tissue ingrowth. Nevertheless, this dual structure, which may only be visible on a microscopic scale, presents concerns about identifying and maintaining the side orientation of the ADM, i.e., during a surgical procedure.

Figure 4:
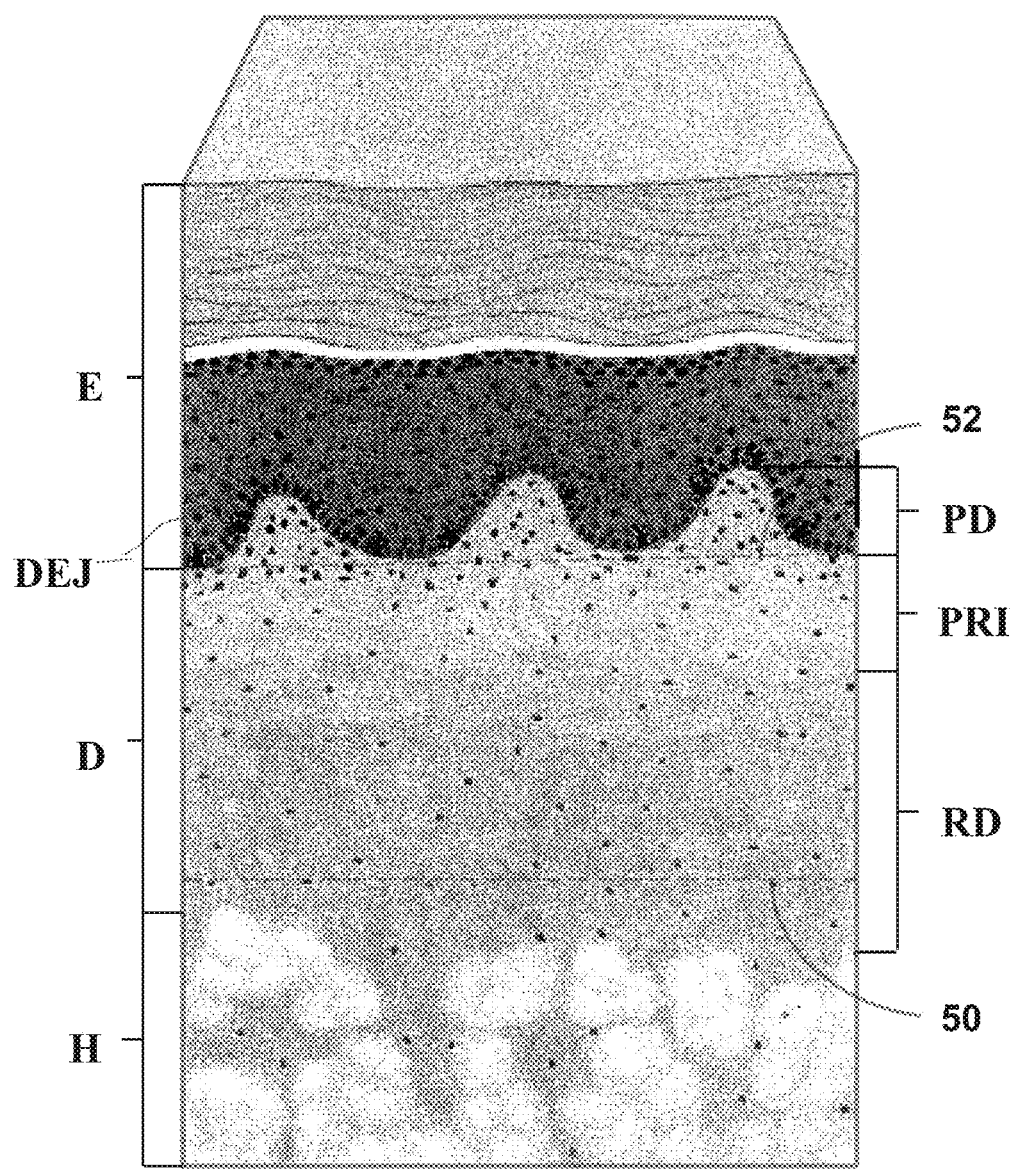
FIG. 4 is perspective schematic view of the section of human skin shown in FIG. 3, showing the cutting steps performed according to an improved fabrication process to produce improved ADMs.

In an improved fabrication process, an ADM is derived from allograft dermal tissue that is recovered from deeper within the dermis, and is therefore farther from, and not adjacent the epidermis. Recovery of portions of the dermis D from the skin suitable for making such ADMs may be accomplished by various techniques and devices, such as, for example, a manual dermatome technique, or dissection with a scalpel. In an improved fabrication process illustrated in FIG. 4, a first cut 50 is made into the reticular dermis RD of the skin (e.g., a section of skin cut from the entire donor skin) proximate the underlying hypodermis H in order to remove it from the dermis D. A second cut 52 is then made into the epidermal portion of the papillary dermis PD containing the dense collagen matrix, as discussed above, in order to remove the epidermis E, the DEJ, and the underlying epidermal portion of the papillary dermis PD. The remaining portion of the dermis D (i.e., the deeper dermal portion of the papillary dermis PD and the reticular dermis RD) constitutes a collagen matrix ("the tissue") having substantially uniform density and porosity.

This remaining portion of the dermis, i.e., the tissue, may then be minimally processed, e.g., according to the process disclosed in U.S. Pat. No. 7,723,108, the disclosure of which is incorporated by reference herein in its entirety. Alternatively, the tissue may be decellularized by chemically treating it with saline, detergent, peracetic acid, ethanol and propylene glycol. The tissue may then be washed with sterile water to remove residual processing chemicals. The resulting disinfected and acellular tissue (ADM) may be cut into rectangular-shaped sheets suitable for clinical uses. The tissue sheets may be further treated with aqueous ethanol and packaged to provide a hydrated ADM.

The ADM derived using the improved process(es) disclosed above exhibits properties that are ideal for its use as a sling in breast reconstruction, and its use in other plastic surgery applications. Use of this improved ADM minimizes adhesions and foreign body reactions while promoting vascularization, cellular attachment, and tissue ingrowth at the surgical site. Compared to the previously known ADMs (i.e., described above), this improved ADM possesses more uniform tensile properties (i.e., strength, pliability, stretchability and handling characteristics) that are optimal for its use in breast reconstruction and other plastic surgery applications. This improved ADM also possesses improved suture retention strength, and elasticity and deformability that are optimal for its intended use. For example, the improved elasticity of this improved ADM promotes better expansion of the tissue in breast reconstruction. This improved ADM is therefore very strong and closely mimics the biomechanical properties of the tissue that it is intended to replace. Further, this improved ADM is resistant to bacterial colonization and non-immunogenic, as a result of the treatment thereto and decellularization thereof.

Figure 5A:
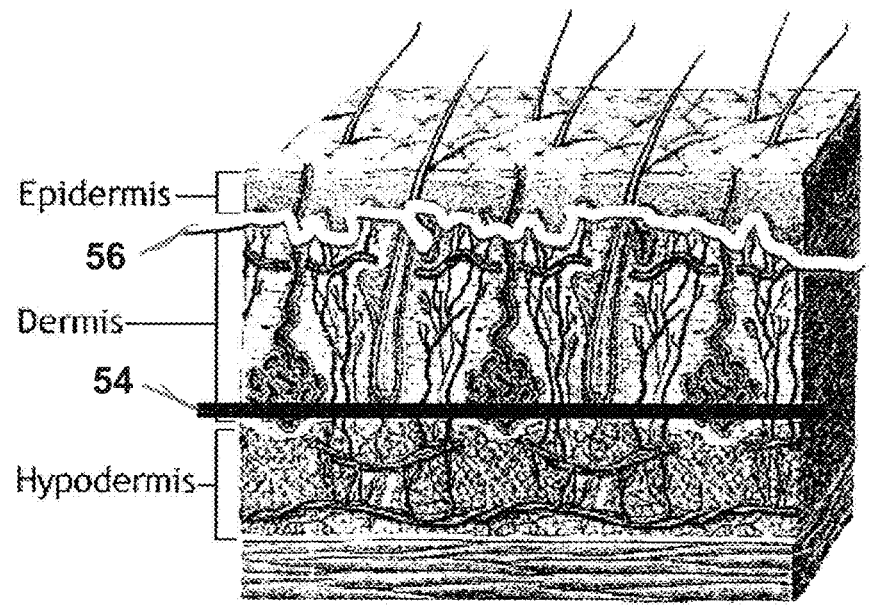
FIG. 5a is a perspective schematic view of a section of human skin showing where cuts may be made according to a previously known fabrication process for preparing ADMs useful for making soft tissue repair grafts as described herein.

FIG. 5a illustrates a previously known process for fabricating the previously known ADMs, including those commercially available under the names FlexHD® Structural™ ADM, AlloDerm® ADM and AlloDerm® RTU ADM), namely, cutting the lower portion of the dermis and hypodermis (represented by straight line 54), and chemically treating the tissue to remove only the epidermis (represented by uneven line 56) and expose the DEJ.

Figure 5B:
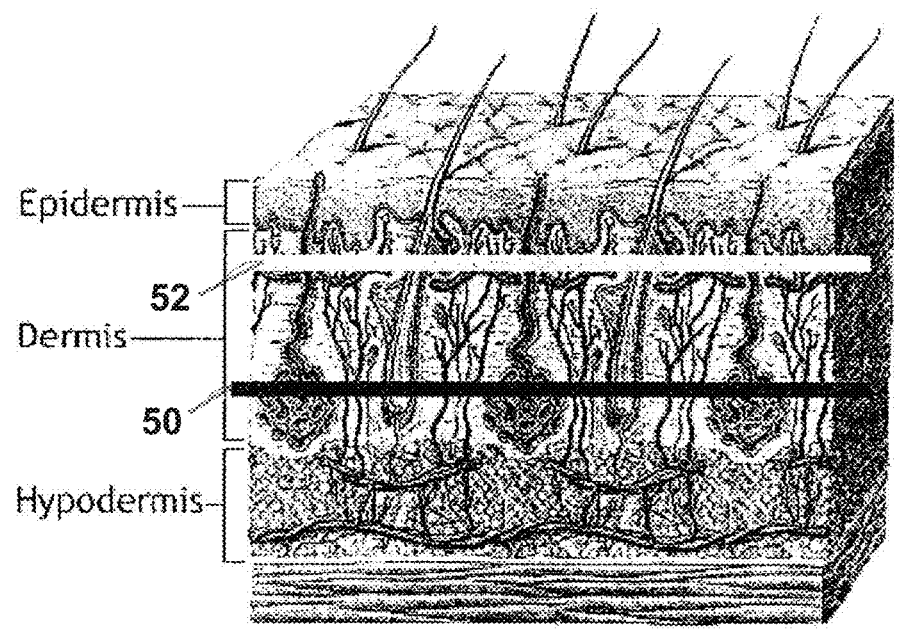
FIG. 5b is a perspective schematic view of a section of human skin showing where cuts may be made according to an improved process for preparing ADMs useful for making soft tissue repair grafts as described herein.

FIG. 5b illustrates the improved fabrication process mentioned hereinabove which produces improved ADMs having more uniform density and porosity, namely, the lower portion of the dermis and hypodermis are cut (represented by straight line 50), and then a second cut (represented by straight line 52) is made deeper into the dermis than the aforementioned chemical treatment used to fabricate previously known ADMs. In one embodiment of the alternative fabrication process, for example, the second cut results in the removal of the epidermis, the DEJ, and the upper, epidermal portion of the papillary dermis. As mentioned above, the substantially uniform density and porosity of the improved ADMs produced by this alternative fabrication process promotes more rapid and efficient cellular ingrowth equally from either side of the ADM grafts as compared to the previously known ADMs (i.e., the FlexHD Structural® ADM, FlexHD Pliable® ADM, AlloDerm® ADM and AlloDerm® RTU ADM).

It will be understood that the embodiments of the present invention described hereinabove are merely exemplary and that a person skilled in the art may make variations and modifications without departing from the spirit and scope of the invention. All such variations and modifications are intended to be included within the scope of the present invention.

EXAMPLES

Example 1: Surgical Placement of an ADM Graft During Pre-Pectoral Breast Reconstruction The graft is suitable for use in pre-pectoral breast reconstruction procedures and:
  is made of ADM;
  has a vertical axis V and a horizontal axis H, where the ratio of the length of the vertical axis to the length of the horizontal axis is 1.15;
  is symmetrical about its vertical axis;
  has three notches (i.e., at 9, 12 and 3 o'clock positions on the peripheral edge of the graft);
  has three cuff elements formed by the three notches;
  has a focal point positioned at the midpoint of the horizontal axis and at a point on the vertical axis which is 45% above the bottommost point on the peripheral edge of the graft;
  has a plurality of slits which form a plurality of circular patterns which are concentric about the focal point.

In use, the foregoing ADM graft is placed and secured within a reconstructed breast to support a breast implant positioned anteriorly to the chest muscles of a patient during a pre-pectoral breast reconstruction procedure. The following steps are performed:

1. Make markings on the breast and draw horizontal and vertical lines centered around the nipple, mark inframammary fold, medial, lateral and superior portions of the breast to outline the breast footprint;
2. Prepare the Breast Pocket with hemostasis and irrigation;
3. Place pocket defining sutures in the lateral aspect and inframammary fold;
4. Use a breast implant sizer to determine the appropriate implant volume;
5. Mark the medial and lateral borders of the implant sizer in the breast pocket;
6. Mark the superior and midpoint of the breast to define the position on the breast at which the topmost (superior) point (34) of the graft, which is proximate the top notch 14, will be anchored
7. Triple wash the ADM graft with triple antibiotic solution alternating with betadine and squeeze excess fluid out of the ADM graft (a suitable triple antibiotic solution includes a mixture of 1 gram of cefazolin, 80 milligrams of gentamicin, and 50,000 International Units of bacitracin, in 500 milliliters of normal saline;
8. Mark the ADM graft to establish the X (i.e., horizontal H) axis by connecting the notches at points 38 and 40 and Y (i.e., vertical V) axis by drawing a perpendicular line starting at the superior notch at topmost point 34. Marking of these axes allows for orientation of the ADM graft by correlating the markings on the ADM graft to the external markings on the patient's skin, thereby facilitating symmetrical inset and positioning of the ADM graft into breast pocket;
9. Drape the ADM graft over the implant sizer and mark the edge of the implant circumferentially on the ADM graft adjusting the folds (e.g., at imaginary arcuate lines 26, 28, 30 on the graft 10, see FIG. 1) and widths of the cuff elements to the size of the implant;
10. Fold the cuff elements (edges) of the ADM graft according to the markings then carefully place the marked ADM into the prepared breast pocket without touching the skin;
11. Adjust the ADM graft position accordingly by correlating the external markings of the aforesaid axes;
12. Find the superior point of the Y (vertical V) axis at the top of the pectoralis (Point A, e.g., the a topmost (i.e., superior) point 34 of the ADM graft, see FIGS. 1 and 2C);
13. Use a continuous 2-0 Monocryl (a commercially available suture manufactured and marketed by Ethicon of Cornelia, Ga., USA) to suture the medial edge of the ADM graft to the muscle from Point (A) to a Point (B) proximate to or on the inframammary fold, leaving an opening at the inferior edge of adequate size for insertion of the implant or tissue expander;
14. Use a continuous 2-0 Monocryl to suture the lateral edge of the ADM to the muscle, again starting from Point (A), and continuing to a Point (C), which is proximate to or on the inframammary fold and some distance away from Point (B), thereby leaving an opening adequate for placement of the implant or tissue expander;
15. Inject a pain relief agent (e.g., Exparel commercially available from Pacira Pharmaceuticals of Parsippany, N.J., USA) circumferentially to provide an long lasting intercostal block;
16. Open the final, permanent breast implant (I) and wash in the triple antibiotic solution;
17. Change gloves and place the permanent breast implant into the breast pocket utilizing a Keller funnel no touch technique;
18. Use a ribbon to protect and retract the implant while interrupted suture 2-0 Monocryl sutures are placed to close the aforesaid opening of the breast pocket at the inframammary fold;
19. Place two drains at the lateral aspect of the inframammary fold incision; and
20. Suture the incision in three layers using 2-0 Moncryl deeper interrupted sutures, followed by 3-0 Moncryl dermal and subcuticular sutures.

The invention claimed is:
1. A graft for treating a breast of a patient, wherein the breast has contours, the graft is planar prior to placement in the patient and comprises:
an arcuate peripheral edge defining a generally circular or slightly oval shape with a geometric center;
a focal point located at or near the geometric center; and
a plurality of slots extending entirely through the graft and forming two or more circular patterns which are spaced apart and concentric about the focal point,
wherein the graft is sized and shaped for treating the breast and further comprises an imaginary vertical axis intersecting the arcuate peripheral edge at a topmost point and an oppositely positioned bottommost point, passing through the focal point and having a total vertical distance measured between the topmost and bottommost points; wherein a distance between the bottommost point and the focal point is from about 40% to about 50% of the total vertical distance.
2. The graft of claim 1, wherein when the graft is positioned proximate to or in place of the breast being treated, the plurality of slots permit expansion and reshaping of the graft into a three dimensional structure which conforms to the contours of the breast being treated with minimal tearing of the graft and minimal puckering of the graft or surrounding body tissues.
3. The graft of claim 1, wherein the distance between the bottommost point and the focal point is about 45% of the total distance.
4. The graft of claim 1, wherein when the graft is positioned proximate to or in place of the breast being treated which has or had a natural nipple position, the focal point F is positioned underneath and adjacent the natural nipple position.
5. The graft of claim 1, further comprising an imaginary horizontal axis intersecting the arcuate peripheral edge at first and second farthest and oppositely positioned points, passing through the focal point such that the vertical and horizontal axes intersect one another at the focal point, and having a horizontal length measured between the first and second farthest and oppositely positioned points, wherein the vertical length is the same as or greater than the horizontal length.
6. The graft of claim 1, further comprising:
a plurality of notches, each notch being positioned on the arcuate peripheral edge to provide guidance to a user for properly orienting the graft relative to the body feature being treated, the plurality of notches comprising:
a first notch positioned at the first farthest and oppositely positioned point;
a topmost notch positioned at the topmost point of the graft, wherein when the graft is in a preferred orientation relative to the body feature being treated, the topmost notch will be aligned with a superior point of the body feature;
a second notch positioned at the second farthest and oppositely positioned point;
a plurality of cuff elements, each of which has a width measured from the arcuate peripheral edge, toward the geometric center, to an imaginary arcuate line on the graft, wherein, when the cuff elements are folded at the imaginary arcuate line, a reinforced folded edge is formed for affixing the graft to surrounding body tissue of the patient, the plurality of cuff elements comprising:
a first cuff element defined by and extending between the first and topmost notches;
a second cuff element defined by and extending between the topmost and second notches;
a third cuff element defined by and extending between the first and second notches.
7. A surgical method for treating a breast of a patient, wherein the breast has contours, the surgical method comprising:

positioning the graft of claim 1 within the patient proximate to or in place of the breast being treated, and affixing the graft to surrounding body tissues in a manner which permits expansion and reshaping of the graft into a three dimensional structure which conforms to the contours of the breast being treated.

8. A graft of for treating a body feature of a patient, wherein the body feature has contours, the graft is planar prior to placement in the patient and comprises:

an arcuate peripheral edge defining a generally circular or slightly oval shape with a geometric center;

a focal point located at or near the geometric center;

a plurality of slots extending entirely through the graft and forming two or more circular patterns which are spaced apart and concentric about the focal point, and a cuff element extending along at least a portion of the arcuate peripheral edge and having a width measured from the arcuate peripheral edge, toward the geometric center, to an imaginary arcuate line on the graft, wherein when the cuff element is folded at the imaginary arcuate line a reinforced folded edge is formed for affixing the graft to surrounding body tissue of the patient.

9. The graft of claim 8, wherein the graft is sized and shaped for treating a body feature selected from: a breast, a knee, an elbow, a chin, a fingertip, a toe, a heel, a foot, and buttocks.

10. The graft of claim 8, further comprising at least one notch positioned on the arcuate peripheral edge to provide guidance to a user for properly orienting the graft relative to the body feature being treated.

11. A graft for treating a body feature of a patient, wherein the body feature has contours, the graft is planar prior to placement in the patient and comprises:

an arcuate peripheral edge defining a generally circular or slightly oval shape with a geometric center;

a focal point located at or near the geometric center;

a plurality of slots extending entirely through the graft and forming two or more circular patterns which are spaced apart and concentric about the focal point, and at least one notch positioned on the arcuate peripheral edge to provide guidance to a user for properly orienting the graft relative to the body feature being treated.

12. The graft of claim 11, wherein the at least one notch comprises a plurality of notches, each of which is positioned on the arcuate peripheral edge and which are spaced apart from one another to provide guidance to a user for properly orienting the graft relative to the body feature being treated.

13. A graft for treating a body feature of a patient, wherein the body feature has contours, the graft is planar prior to placement in the patient and comprises:

an arcuate peripheral edge defining a generally circular or slightly oval shape with a geometric center;

a focal point located at or near the geometric center; and a plurality of slots extending entirely through the graft and forming two or more circular patterns which are spaced apart and concentric about the focal point, wherein the graft is formed from a biocompatible material comprising an acellular dermal matrix which comprises a dermal tissue consisting essentially of a portion of a papillary dermis and at least a portion of a reticular dermis, and essentially lacking an epidermis, a dermis-epidermis junction, a portion of papillary dermis proximate the dermis-epidermis junction and a hypodermis.

14. A graft for treating a body feature of a patient, wherein the body feature has contours, the graft is planar prior to placement in the patient and comprises:

an arcuate peripheral edge defining a generally circular or slightly oval shape with a geometric center;

at least one cuff element extending along at least a portion of the arcuate peripheral edge and having a width measured from the arcuate peripheral edge, toward the geometric center, to an imaginary arcuate line on the graft, wherein, when the at least one cuff element is folded at the imaginary arcuate line, a reinforced folded edge is formed for affixing the graft to surrounding body tissue of the patient.

15. The graft of claim 14, further comprising at least one notch positioned on the arcuate peripheral edge to provide guidance to a user for properly orienting the graft relative to the body feature being treated.

16. A surgical method for treating a body feature of a patient, the surgical method comprising:

positioning the graft of claim 14 within the patient proximate to or in place of the body feature being treated, and affixing the graft to surrounding body tissues.

17. A graft for treating a body feature of a patient, wherein the graft is planar prior to placement in the patient and comprises:

an arcuate peripheral edge defining a generally circular or slightly oval shape with a geometric center; and at least one notch positioned on the arcuate peripheral edge to provide guidance to a user for properly orienting the graft relative to the body feature being treated.

18. The graft of claim 17, wherein one of the at least one notches is located at a topmost point on the graft and, when the graft is in a preferred orientation relative to the body feature being treated, the notch will be aligned with a superior point of the body feature.

19. A surgical method for treating a body feature of a patient, the surgical method comprising:

positioning the graft of claim 17 within the patient proximate to or in place of the body feature being treated, and affixing the graft to surrounding body tissues.

* * * * *